United States Patent [19]

Goedecke

[11] Patent Number: 5,675,084
[45] Date of Patent: Oct. 7, 1997

[54] METHOD AND DEVICE FOR TESTING GAS CARRYING PIPELINES

[75] Inventor: Hartmut Goedecke, Weilburg/Kubach, Germany

[73] Assignee: Pipetronix GmbH, Stutensee, Germany

[21] Appl. No.: 593,048

[22] Filed: Jan. 29, 1996

[30] Foreign Application Priority Data

Jan. 30, 1995 [DE] Germany ............ 195 02 764.7

[51] Int. Cl.$^6$ ............................................. G01N 29/06
[52] U.S. Cl. ................... 73/623; 73/644; 73/866.5; 73/592
[58] Field of Search .................. 73/592, 40.5 A, 73/40.5 R, 623, 866.5, 40.5 P, 622, 644, 865.8

[56] References Cited

U.S. PATENT DOCUMENTS

| 2,723,357 | 11/1955 | Van Valkenburg et al. | 73/623 |
|---|---|---|---|
| 3,400,574 | 9/1968 | Cramer | 73/40.5 P |
| 3,533,447 | 10/1970 | Moore | 73/40.5 P |
| 4,945,775 | 8/1990 | Adams et al. | 73/865.8 |
| 5,495,750 | 3/1996 | Dufresne | 73/40.5 R |

FOREIGN PATENT DOCUMENTS

| 149589 | 12/1978 | Japan | 73/623 |
|---|---|---|---|
| 13333 | 1/1982 | Japan | 73/40.5 P |
| 147051 | 9/1982 | Japan | 73/623 |
| 44656 | 3/1984 | Japan | 73/623 |
| 246647 | 11/1986 | Japan | 73/40.5 P |

*Primary Examiner*—Hezron E. Williams
*Assistant Examiner*—Nashmiya Ashraf
*Attorney, Agent, or Firm*—Antonelli, Terry, Stout & Kraus, LLP.

[57] ABSTRACT

For reducing the coupling liquid carried along during the performance of a test run of a device for testing gas carrying pipelines, the invention provides an ultrasonic gas carrying pipeline testing method, in which an overpressure is produced in a space containing a sensor carrier with ultrasonic sensors and a coupling liquid defined by the pipeline wall and scraper sleeves. An ultrasonic gas carrying pipeline testing device with a sensor carrier and a scraper sleeve positioned upstream thereof and connected thereto is characterized in that a connecting line (24) provided with a pump (26) passes from an area upstream of the scraper sleeve (22) to an area downstream of said scraper sleeve (22).

12 Claims, 1 Drawing Sheet

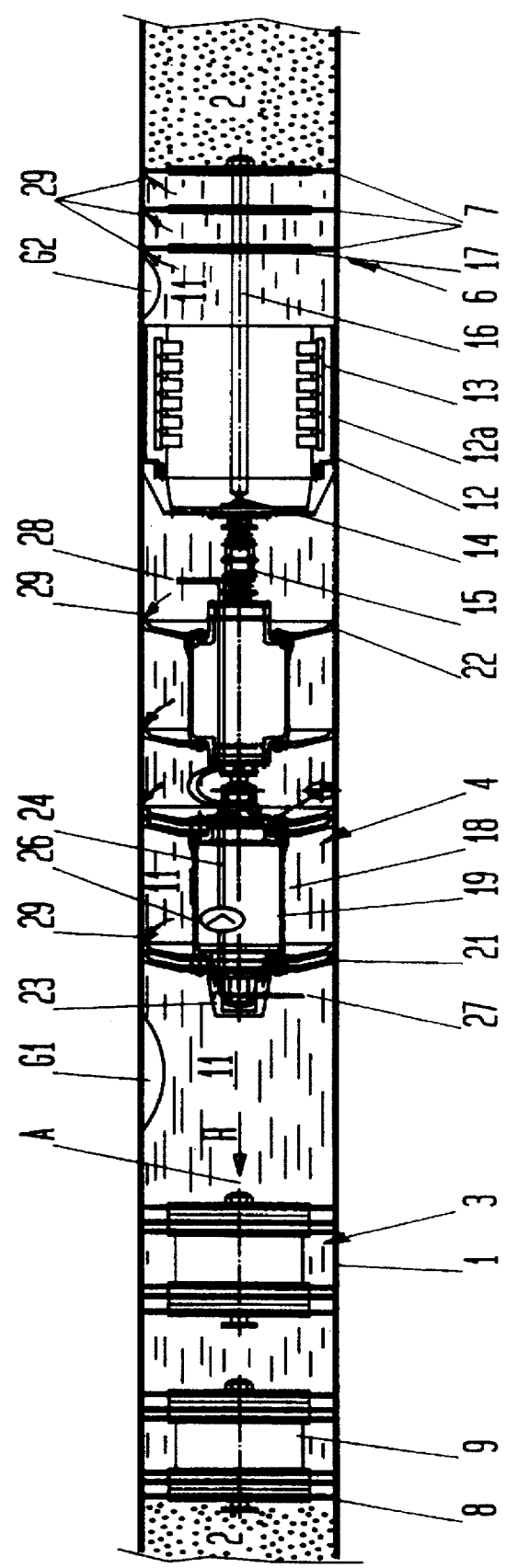

METHOD AND DEVICE FOR TESTING GAS CARRYING PIPELINES

FIELD OF THE INVENTION

The invention relates to a method for testing gas carrying pipelines by means of ultrasonics, as well as to a device for testing gas carrying pipelines by ultrasonics, having a sensor carrier and a scraper sleeve positioned behind the same and connected thereto.

BACKGROUND OF THE INVENTION

Ultrasonic material testing requires a coupling fluid or liquid. For the ultrasonic testing of gas carrying pipelines it is consequently necessary for the sensors and therefore also a sensor carrier carrying the same to be immersed in said fluid or liquid. Thus, in the case of a test run of a device for ultrasonic testing through the gas carrying pipeline it is necessary to carry along a liquid plug known as a batch. According to the prior art the plug or batch is carried along in that at a considerable distance upstream and downstream of the actual measuring device are carried along separating scrapers provided with sealing sleeves and which enclose between them the liquid plug and the ultrasonic measuring device (ultrasonic scraper).

Such a liquid plug or batch must have a considerable length. With standard distances of several hundred kilometers, the batch length must be 200 to 2000 m. A conventional batch construction has, in front of the actual measuring scraper, four or five separating scrapers with mutual spacings of 20 to 100 m and behind the measuring scraper there are at least two separating scrapers with a corresponding relative spacing. The distance between the measuring scraper and the next separating scraper upstream thereof is e.g. 200 m and behind it the following separating scraper is located at a distance of 600 m, so that the total length is approximately 1000 m. In particular the distance between the measuring scraper and the first following separating scraper is important, because as a result of the liquid path through the pipeline there would otherwise be a risk of the following separating scraper being pressed during the run against the measuring scraper and as a result the sensor means located at its rear end would be damaged or destroyed. The necessarily large liquid quantity for performing a test run is associated with significant disadvantages, particularly for the pipeline operator. Thus, a considerable liquid mass must be introduced into the gas carrying pipeline, which involves high costs for acquisition and introduction, high costs for the actual liquid material and high costs for the disposal thereof, because the liquid is contaminated on forcing through the pipeline.

Therefore the problem of the invention is to provide a method and a device for testing gas carrying pipelines by ultrasonics avoiding the aforementioned disadvantages and in particular permitting the carrying out of the testing with a much smaller liquid quantity.

SUMMARY OF THE INVENTION

According to the invention the set problem is solved in the case of a method of the aforementioned type in that an overpressure is produced in a space defined by the pipeline wall and scraper sleeves and which contains a sensor carrier with ultrasonic sensors and a coupling liquid. A device according to the invention solves the problem in that a connecting line provided with a pump passes from an area upstream of the scraper sleeve to an area downstream of said scraper sleeve.

As a result of the measures according to the invention the sensor carrier of the device carrying the ultrasonic sensors is always located in a liquid plug or batch, which has an overpressure with respect to other areas of the carried along batch, particularly upstream of said scraper sleeve, but also with respect to following scraper sleeves. This reduces the risk of gas bubbles forming in the area where the sensor carrier is located. Gas bubbles penetrating or forming therein can be rapidly moved out of the area by the overpressure. This is in particular assisted by the fact that the scraper and/or sealing sleeves have in their upper area a liquid passage and either the liquid passage is formed by reducing the material thickness of the scraper and/or sealing sleeves in their circumferential area or an axial notch is provided in the upper circumferential sleeve area.

According to another development of the invention, an inlet of the connecting line issues below a central axis of the device, which increases the probability of the pump only sucking liquid out of the space upstream of the scraper.

According to another development of the invention the connecting line is guided by two spaced, succeeding scraper sleeves both located upstream of the sensor carrier. In preferred manner there are sealing sleeves located behind and axially connected to the sensor carrier. If the sealing sleeves following the sensor carrier are connected thereto by a rigid, axial device (even though Jointed movable), then a running up or abutting of the sealing sleeves on the sensor carrier and therefore damage thereto is avoided.

Due to all these measures the length of the batch to be carried along can be considerably reduced. A typical total device for the batch required in the device according to the invention from the furthest forward separating scraper to the rear sealing sleeve is approximately 50 to 100 m for roughly the same length of run as mentioned hereinbefore.

BRIEF DESCRIPTION OF THE DRAWINGS

Further advantages and features of the invention can be gathered from the claims and the following description of an embodiment of the device according to the invention with reference to the single drawing showing a preferred construction of the device for testing gas carrying pipelines according to the invention.

DETAILED DESCRIPTION OF THE EMBODIMENT

The drawing shows a pipeline 1 carrying a gas 2. If the pipeline is to be ultrasonically tested for faults such as corrosion, cracks, etc., then in per se known manner a separating scraper 3 is provided. In the flow direction R of the gas behind the separating scraper 3 is provided a device for testing gas carrying pipelines 1 according to the invention, or an ultrasonic scraper 4 for short. In the represented embodiment the scraper 4 carries on its end (at 6) which is at the rear in the flow direction R and remote from the separating scraper 3, sealing sleeves 7, here in the form of sealing disks.

The separating scraper 3 also has sealing sleeves or disks 8, as well as a sleeve carrier 9 carrying the same. Between the separating scraper 3 and the sealing sleeves 7 is provided a liquid 11 as the coupling medium for the ultrasonics used for testing the pipeline. The sealing sleeves 7, 8 seal the liquid forming a plug in the pipeline 1 with respect to the gas 2 conveyed through the pipeline 1 upstream of the separating scraper 3 and downstream of the sealing sleeves 7.

Such an arrangement with a liquid plug or batch with respect to the sealing sleeves to be sealed against the surrounding gas and a measuring or test scraper located between them is referred to hereinafter as a batch.

The device according to the invention, i.e. the scraper 4, has a sensor carrier 12 with ultrasonic sensors 13. The sealing sleeves 7 are connected in jointed manner by means of a joint 14 to the sensor carrier 12, but with a fixed axial spacing, which is defined by a carrier rod 16 on which is firmly positioned the rigid disks 17 carrying the sleeves 7. The sensor carrier 12 with the sensors 13 is constructed in per se known manner, such as is e.g. known from EP 255 619.

Upstream of the sensor carrier 12 and connected thereto by means of a joint 15 is a sleeve carrier 18, which can contain in a casing 19 e.g. all the electronics, storage media, etc. In the represented embodiment the sleeve carrier 18 carries two scraper sleeves 21, 22. At its front end (in the flow direction R) it is provided with a run-up or abutting protection means 23, which prevents damage to the components of the scraper 4 if the liquid between it and the separating scraper 3 during the operation of the scraper is reduced to such an extent that the test scraper 4 strikes against the separating scraper 3.

From the area upstream of the front scraper sleeve 21 to the area behind the rear scraper sleeve 22 (considered in the flow direction R) extends a connecting line 24 containing a pump 26, which pumps liquid through the connecting line from the area between the separating scraper 3 and the front scraper sleeve 21 into the area between the rear scraper sleeve 22 and the rear sealing sleeves 7, in which is located the sensor carrier 12 with the ultrasonic sensors 13.

The intake 27 of the connecting line 24 is located in a lower area of the pipeline 1 or the measuring scraper 4 and certainly below the symmetry axis A of the pipeline 1 or scraper 4. The outlet 28 of the connecting line 24 is in the area between the rear scraper sleeve 22 and the front sealing sleeves 7.

At 29 the scraper and sealing sleeves 21, 22, 7 have no liquid passages. They can be formed by weakening the sleeve circumference or a small V-shaped notch in the circumferential area of the sleeves 7, 21, 22.

The drawing also shows gas bubbles G1 and G2. It is pointed out that the sensor carrier 12 in its axially parallel area 12a, which carries the sensors 13, can either have longitudinal grooves in the outer area or the carrier can be constructed as individual fingers or arms with radial openings between them.

During the operation of the complete means 3, 4 liquid is permanently pumped by the pump 26 from the space upstream of the test scraper 4 into the space around the sensor carrier 12 with its sensors 13 and an overpressure is built up in said space. Due to the fact that the liquid is sucked via the intake 27 in the lower area of the pipeline 1 and the said overpressure is produced in the vicinity of the sensor carrier, it is ensured that in the latter there are no gas bubbles or the gas bubbles which occur, such as the gas bubble G2, are forced out of the space surrounding the sensor carrier 12 through the weakening areas 29 of the sleeves 22, 21 and 7. It is thereby ensured that the gas bubbles do not stop along the space surrounding the sensor carrier 12 and in particular between the sensors 13 and the wall of the pipeline 1 and therefore make difficult or even impossible for a long period time the measurements and tests. In addition, through the overpressure produced in the described manner in the space surrounding the sensor carrier 12 it is ensured that no gas bubbles, such as a gas bubble G1, can penetrate the liquid upstream of the device or scraper 4 according to the invention. Such gas bubbles G1, G2 can be formed through branches in the pipeline into which water can be splashed during the moving past of the device, so that gas is carried along in the batch.

Due to the indicated measures and the resulting gas bubble check, it is ensured that all the coupling liquid carried along through the device for a predetermined distance can be much smaller than is the case in conventional ultrasonic testing devices for gas carrying pipelines, where there are several separating scrapers upstream and downstream of the testing device must have a larger spacing. As a result of the axially fixed connection of the rear sealing sleeve 7 with the testing device a significantly greater liquid extension length behind the measuring device 4 is avoided, this being needed in the known devices to prevent a running up of the rear separating scrapers onto the test scraper, because this could lead to the destruction thereof.

I claim:

1. Device for testing a gas-carrying pipeline by ultrasound, the device having an ultrasonic pig freely movable through the pipeline to be tested, the ultrasonic pig having a sensor carrier to move through the pipeline and at least one scraper sleeve, the sensor carrier carrying ultrasonic sensors and the at least one scraper sleeve being positioned upstream of the sensor carrier and connected with the sensor carrier, the ultrasonic pig being further provided with a liquid conducting tube having an inlet upstream of the at least one scraper sleeve within the pipeline to be tested and an outlet downstream of said at least one scraper sleeve, the device further having a pump, to move through the pipeline, and the pump is provided between the inlet and the outlet of said tube on the movable ultrasonic pig to pump liquid in the pipeline from upstream of the at least one scraper sleeve to the outlet.

2. Device according to claim 1, wherein said inlet issues below a central axis of the ultrasonic pig.

3. Device according to claim 1 or 2, wherein the sensor carrier has an axis, and wherein the ultrasonic pig further includes at least one sealing sleeve positioned behind and connected to the sensor carrier on the axis of the sensor carrier.

4. Device according to claim 3, wherein said outlet issues in an area between a rear scraper sleeve, of the at least one scraper sleeve, and a first sealing sleeve, of the at least one sealing sleeve, connected to said sensor carrier.

5. Device according to claim 3, wherein at least one structure of (1) said at least one scraper sleeve and (2) said at least one sealing sleeve is provided with liquid passages in upper areas of the at least one structure.

6. Device according to claim 5, wherein said liquid passages are formed by reduction of material thickness of the at least one structure in a circumferential area of the at least one structure.

7. Device according to claim 5, wherein said liquid passages are constituted by axial notches provided in upper circumferential areas of the at least one structure.

8. Device according to claim 3, wherein said at least one sealing sleeve is held on a carrier rod such that there is a fixed axial spacing between the sensor carrier and the at least one sealing sleeve.

9. Device according to claim 1 or 2, wherein said tube passes through more than one spaced, successive scraper sleeve located upstream of the sensor carrier.

10. Device according to claim 1, wherein said pump is battery powered.

11. Device according to claim 1, wherein said pump is driven by friction wheels.

12. Device according to claim 1, wherein said inlet is positioned in such a way that the inlet remains in a position below a central axis of the ultrasonic pig even when a scraper is rotating about a longitudinal axis of the scraper.

* * * * *